United States Patent [19]

Kreutner et al.

[11] Patent Number: 4,564,626

[45] Date of Patent: Jan. 14, 1986

[54] METHODS OF INDUCING BRONCHODILATION

[75] Inventors: William Kreutner, West Caldwell; Marvin I. Siegel, Florham Park, both of N.J.

[73] Assignee: Schering Corporation, Kenilworth, N.J.

[21] Appl. No.: 481,503

[22] Filed: Apr. 1, 1983

[51] Int. Cl.[4] ...................... A61K 31/35; A61K 31/38
[52] U.S. Cl. .................................. 514/430; 514/455; 514/649
[58] Field of Search ................ 424/282, 283; 514/455, 514/430

[56] References Cited

U.S. PATENT DOCUMENTS

| | | | |
|---|---|---|---|
| 3,922,345 | 11/1975 | Lipinsky et al. | 424/251 |
| 4,118,506 | 10/1978 | Bhat et al. | 424/283 |
| 4,134,986 | 1/1979 | Bajwa et al. | 424/283 |
| 4,275,219 | 6/1981 | Zupan | 560/29 |

OTHER PUBLICATIONS

Bhat et al., *J. C. S. Perkin I*, 767, (1982).
Metzger et al.,–*Arzneimittel-Forsch., (Drug Res.,* 31, (II), 1248, (1981).
Foye (Ed.), *Principles of Medicinal Chemistry*, pp. 802–803, 1976.
Litosch et al., Molec. Pharmacol. 22: 109–115, (1982).
Tipton et al., "Dynamics of Isoproterenol Subsensitivity in Guinea Pig Airway Smooth Muscle," *Lung*, vol. 159, pp. 199–210, (1981).
Burka et al., "Bronchodilator-Mediated Relaxation of Normal and Ovalbumin-Sensitized Guinea-Pig Airways: Lack of Correlation with Lung Adenylate Cyclase Activation," *Br. J. Pharmac.,* vol. 83, pp. 645–655, (1984).
Kolbeck et al., "Apparent Irrelevance of Cyclic Nucleotides to the Relaxation of Tracheal Smooth Muscle Induced by Theophylline," *Lung*, vol. 156, pp. 173–183, (1979).
Mitchell et al., "In Vitro Action of Combined Salbutamol and Theophylline on Anaphylactic Contraction Mediator Release and Cyclic 3', 5'-Adenosine Monophosphate in Lung Parenchyma," *European Journal of Pharmacology*, vol. 57, pp. 399–406, (1979).
Vargaftig et al., "Enhancement by Prostacyclin of the Contractility of the Guinea Pig Airways Smooth Muscle," *European Journal of Pharmacology*, vol. 74, pp. 141–148, (1981).
Burka, J. F., "Effects of Selected Bronodilators on Antigen-and A23187-Induced Contraction of Guinea--Pig Trachea," *The Journal of Pharmacology and Experimental Therapeutics*, vol. 225, No. 2, pp. 427 et seq. (1983).
Katsuki et al., "Regulation of Adenosine Cyclic 3', 5'-Monophosphate and Guanosine Cyclic 3', 5'-Monophosphate Levels and Contractility in Bovine Tracheal Smooth Muscle," *Molecular Pharmacology*, vol. 13, pp. 330–341, (1977).

*Primary Examiner*—Leonard Schenkman
*Attorney, Agent, or Firm*—James R. Nelson; Stephen I. Miller; Gerald S. Rosen

[57] ABSTRACT

A method for producing bronchodilation in a mammal is disclosed. Composition for use in said method are also described.

2 Claims, No Drawings

METHODS OF INDUCING BRONCHODILATION

BACKGROUND OF THE INVENTION

The compound forskolin and certain derivatives possess activity as bronchodilators. The clinical usefulness of forskolin as a bronchodilator may be potentially limited, however, since this compound also displays positive inotropic and chronotropic effects at dose levels which produce bronchodilation. It would therefore be desirable to provide a means whereby forskolin and its derivatives could be utilized to produce bronchodilation without producing unwanted cardiac effects.

SUMMARY OF THE INVENTION

The invention sought to be patented in its pharmaceutical composition aspect is a bronchodilator composition which comprises:

(a) a subthreshold bronchodilating effective amount of forskolin or a forskolin derivative; and
(b) a subthreshold bronchodilating effective amount of a beta adrenergic agonist;

in combination with a pharmaceutically acceptable carrier.

Forskolin is identified by the chemical name, 7β-acetoxy-8,13-epoxy-1α,6β,9α-trihydroxylabd-14-en-11-one [*J. C. S. Perkin,* I 767 (1982)]. For purposes of the invention, the preferred forskolin derivatives are those having the structural formula I.

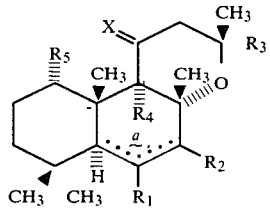

wherein $R_1$ and $R_2$ may be the same or different and are =O, H, or $OR_{11}$ wherein $R_{11}$ is H, carboxylic acyl having from 1 to 6 carbon atoms or

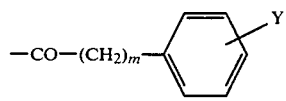

wherein
m is 0, 1, 2 or 3 and Y is hydrogen, halogen, alkyl having from 1 to 6 carbon atoms, alkoxy having from 1 to 6 carbon atoms, alkylthio having from 1 to 6 carbon atoms, OH, $CF_3$, $NO_2$, Cn, phenyl, benzyl, phenoxy or $NR_aR_b$ wherein $R_a$ and $R_b$ are the same or different and are H or alkyl having from 1 to 6 carbon atoms; $R_1$ and $R_2$ when taken together may form

wherein
$R_{13}$ and $R_{14}$ may be the same or different and are H, alkyl having from 1 to 6 carbon atoms, alkenyl having from 2 to 6 carbon atoms, alkynyl having from 2 to 6 carbon atoms or

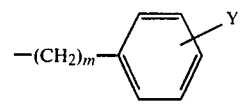

wherein m and Y are defined above;
$R_3$ is hydrogen; alkyl having from 1 to 10 carbon atoms; $CH_2OH$; CHO; $CO_2R_{15}$ wherein $R_{15}$ is H or alkyl having from 1 to 6 carbon atoms;
—CH=$CR_{16}R_{17}$ wherein $R_{16}$ is H, halogen, alkyl having from 1 to 6 carbon atoms,

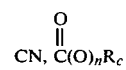

wherein n is 0 or 1 and $R_c$ is H, alkyl having from 1 to 6 carbon atoms, phenyl or benzyl, $CHOHR_c$ or $C(OR_d)_2R_c$ wherein $R_c$ is defined above and $R_d$ is alkyl having from 1 to 6 carbons, $R_{17}$ is H, alkyl having from 1 to 6 carbon atoms, alkoxy having from 1 to 6 carbon atoms, benzyl, phenyl or halogen;
—C≡C—$R_{18}$ wherein $R_{18}$ is H, alkyl having from 1 to 12 carbon atoms, alkoxy having from 1 to 6 carbon atoms or

wherein Y is defined above;
—CHOH—C≡C—$R_{19}$ wherein $R_{19}$ is H, alkyl of from 1 to 6 carbon atoms, phenyl or benzyl;
—CH=C=$CHR_{19}$ wherein $R_{19}$ is defined above;
—CH=N—$OR_{19}$ wherein $R_{19}$ is defined above;

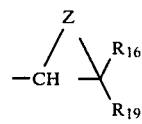

wherein Z is O or S, and $R_{16}$ and $R_{19}$ are defined above;
—$CH(ZR_{20})_2$ wherein Z is defined above and $R_{20}$ is alkyl having from 1 to 6 carbon atoms, phenyl, benzyl or the two groups $R_{20}$ may together form —$(CH_2)_p$— wherein p is 2 or 3;

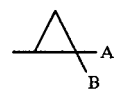

wherein A and B are H, halogen, alkyl having from 1 to 6 carbon atoms, phenyl, benzyl or

wherein n and $R_c$ are defined above;

—CH=N—NDE wherein D and E are H, alkyl having from 1 to 6 carbon atoms, benzyl, phenyl, COG, $SO_2G$, or $CO_2G$ wherein G is alkyl having from 1 to 6 carbon atoms, benzyl or phenyl;

$R_4$ is H or OH;

$R_5$ is OH; or when $R_4$ and $R_5$ are taken together they may form

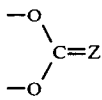

wherein

Z is defined above;

a is an optional bond which may be located in either the 5,6 or 6,7 position; and X is O or H/OH.

More preferred forskolin derivatives are those which have the following values for the above-defined substitents:

$R_1$ and $R_2$ may be the same or different and are $OR_{11}$ wherein $R_{11}$ is defined hereinabove and Y is hydrogen;

$R_3$ is —CH=CHR$_{30}$ wherein $R_{30}$ is hydrogen, alkyl having from 1 to 6 carbon atoms, phenyl, benzyl or $CO_2R_c$;

—C≡CR$_{30}$;

—CHOH—C≡C—R$_{30}$;

—CH=C—CHR$_{30}$;

—CH=N—OR$_{30}$;

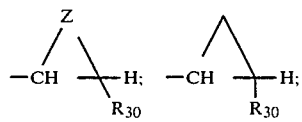

wherein $R_c$ and $R_{30}$ are defined above and

—CH=N—NHR$_{31}$ wherein $R_{31}$ is hydrogen, alkyl having from 1 to 6 carbon atoms, phenyl, benzyl, $SO_2R_{32}$ and $CO_2R_{32}$ wherein $R_{32}$ is alkyl having from 1 to 6 carbon atoms;

$R_4$ is H or OH;

a is either not present or is located in the 5,6 position in which instance $R_1$ is preferably H and $R_2$ is preferably $OR_{11}$ wherein $R_{11}$ is defined hereinabove;

Y is hydrogen; and

X is O.

The term beta adrenergic agonist means a compound which by binding to the appropriate plasma membrane receptor stimulates adenylate cyclase, the enzyme which catalyzes the formation of cyclic-3',5'-adenosine monophosphate (cyclic AMP) from adenosine triphosphate (ATP). See, for example, Weiner, N., Norepinephrine, Epinephrine and the Sympathominetic Amines, in the *Pharmaceutical Basis of Therapeutics* (ed. A. G. Goodman, L. S. Goodman, A. Gilman) Macmillan Publishing, New York, 1980, 6th ed. pp. 138–175.

Examples of such beta adrenergic agonists are isoproterenol, terbutaline, metaproterenol, albuterol and the like. For purposes of the invention the preferred beta adrenergic agonist is albuterol.

The preferred pharmaceutical composition of the invention comprises:

(a) a subthreshold bronchodilating effective amount of forskolin; and (b) a subthreshold bronchodilating effective amount of albuterol;

in combination with a pharmaceutically acceptable carrier.

The invention sought to be patented in its pharmaceutical method aspect is a method for inducing bronchodilation in a mammal which comprises administering:

(a) a subthreshold bronchodilating effective amount of forskolin or a forskolin or a derivative; and (b) a subthreshold bronchodilating effective amount of a beta adrenergic agonist;

to said mammal.

A preferred method of the invention comprises administering the above-defined preferred pharmaceutical composition to said mammal.

DESCRIPTION OF THE INVENTION

The forskolin analogs utilized in the method and compositions of the invention may be prepared by standard procedures. A convenient starting material for preparing these compounds in 7β-acetoxy-8,13-epoxy-1,α,6β,9α-trihydroxylabd-14-en-11-one, Forskolin, [*J.C.S.* Perkin I, 767 (1982)].

Those skilled in the art will recognize that in order to carry out a particular desired synthetic conversion it may be necessary to first protect other reactive sites which may be present in a molecule. Such protection is preferably accomplished by first forming a derivative at the site to be protected which derivative may be readily re-converted to the original functionality, if desired, after the particular synthetic conversion has been carried out. Examples of such protective conversions are esterification of alcohols and ketalization of ketones. Other such conversions will suggest themselves to those skilled in the art. Because such techniques are recognized as within the skill of the art, they are not included in the following description of the preparation of the compounds utilized in the method of the invention.

Compounds wherein $R_1$ is =O may be prepared by oxidizing a corresponding compound wherein $R_1$ is OH. Compounds wherein $R_1$ is $OR_{11}$ may be prepared by acylation of a compound wherein $R_1$ is OH. Compounds wherein $R_1$ is H may be prepared by reduction of a compound wherein $R_1$ is =O.

Compounds having $R_2$ substituents as described herein may be prepared substantially as described hereinabove for a corresponding $R_1$ substituent.

Compounds wherein $R_1$ and $R_2$ together form

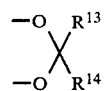

may be prepared by reacting a corresponding compound wherein $R_1=R_2=$ OH with an aldehyde or ketone. Such reactions are generally carried out using conditions whereby the reaction-produced water may be continuously removed.

Compounds having the additional bond, a, may be produced for example by dehydration of a suitable compound wherein $R_1$ and/or $R_2$ are hydroxy.

Compounds wherein $R_3$ is CHO may be prepared from the starting compound (which has a vinyl group at this position) by ozonolysis. Compounds wherein $R_3$ is $CH_2OH$ or $CO_2R_{15}$ may be prepared respectively by reducing or oxidizing the corresponding aldehyde. The carboxylic acid so produced ($R_{15}=H$), thereafter may be esterified if desired. Compounds wherein $R_3$ is —CH=$CR_{16}R_{17}$ may be prepared by treating a compound wherein $R_3$ is CHO with a Wittig reagent, $\phi_3P=CR_{16}R_{17}$. Certain of the substituents, $R_{16}$ and $R_{17}$ may be modified or interconverted subsequent to the Wittig reaction, when desired. Compounds wherein $R_3$ is —C≡C—$R_{18}$ may be prepared by treating a compound wherein $R_3$ is CHO with a reagent $\phi_3P^+CHBrR_{18}$ to produce a bromine containing intermediate which may be dehydrobrominated to produce the desired product. Compounds wherein $R_3$ is C≡CH may be prepared by the addition of bromine to a corresponding compound wherein $R_3$ is —CH=$CH_2$ followed by didehydrobromination. Compounds wherein $R_3$ is —CHOH—C≡C—$R_{19}$ may be prepared from a compound wherein $R_3$ is CHO by treatment with a reagent, MC≡C—$R_{19}$, wherein M is a suitable metal such as lithium. Compounds wherein $R_3$ is —CH=C=$CHR_{19}$ may be prepared from a corresponding compound wherein $R_3$ is —CHOH—C≡C—$R_{19}$ by first esterifying the hydroxyl group and treating the so obtained ester with aluminum chloride. Compounds wherein $R_3$ is —CH=N—$OR_{19}$ may be prepared from a compound wherein $R_3$ is CHO by treatment with a reagent of the formula $H_2N$—$OR_{19}$. Compounds wherein $R_3$ is

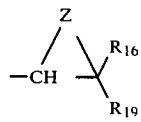

may be prepared from a compound wherein $R_3$ is —CH=$CR_{16}R_{19}$ by treatment with a per acid such as m-chloroperbenzoic acid to produce compounds wherein Z is oxygen, these compounds may be converted to corresponding compounds wherein Z is sulfur by treatment with potassium isothiocyanate. Compounds wherein $R_3$ is —CH($ZR_{20}$)$_2$ may be prepared from a compound wherein $R_3$ is CHO by treatment with an alcohol or thiol using standard procedures. Compounds wherein $R_3$ is

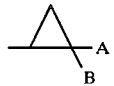

may be prepared by the addition of a dihalocarbene to a compound wherein $R_3$ is —CH=$CH_2$ or by the addition of a methylene carbene to a compound wherein $R_3$ is —CH=CAB. Compounds wherein $R_3$ is —CH=N—NDE may be prepared by treating a compound wherein $R_3$ is CHO with a compound having the formula $H_2N$-NDE using standard procedures.

Compounds wherein $R_4$ is hydrogen may be prepared, for example, by first forming an internal 1,9-carbonate or thiocarbonate ester utilizing a starting material wherein $R_4=R_5=OH$. Convenient reagents for performing these conversions are carbonyl diimidazole or thiocarbonyl diimidazole, respectively. The so produced esters upon treatment with zinc in acetic acid produce the compound wherein $R_4$ is hydrogen and $R_5$ is hydroxy.

The compounds of this invention wherein X is H/OH may be prepared by a suitable reduction of a compound wherein X is =O.

When utilized herein the following terms will have the indicated meanings unless otherwise specified:

alkyl—straight and branched carbon chains having from 1 to 6 carbon atoms;

alkoxy and alkylthio—comprised of straight and branched carbon chains having from 1 to 6 carbon atoms which are singly bonded respectively to an oxygen or a sulfur atom;

halogen—fluorine, chlorine, bromine and iodine;

carboxylic acyl—the acyl portion derived from a straight or branched chain alkanoic acid having from 1 to 6 carbon atoms;

alkenyl—straight or branched carbon chains comprising one double bond and having from 2 to 6 carbon atoms;

alkynyl—straight and branched carbon chains comprising one triple bond and having from 2 to 6 carbon atoms.

The following numbering system is utilized herein for the Forskolin skeleton unless specified othewise:

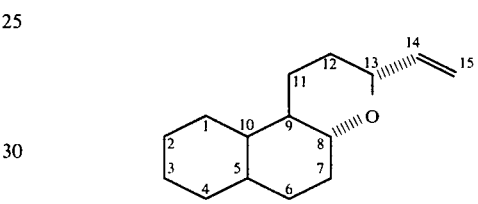

a dashed line ( ) indicates that the substituent is projected below the plane of the paper and is denoted as α; a heavy line ( ) indicates that the substituent is projected above the plane of the paper and is denoted as β.

The active compounds utilized in this invention may exist as solvates, for example as hydrates.

Certain compounds utilized in the invention may exist as optical and/or geometric isomers. For example, substituents and positions 6, 7 and 11 of the forskolin skeleton as well as certain $R_3$ substituents may exist in isometric forms. The invention contemplates all isomers both in pure form and in admixture.

Examples of preferred beta adrenergic agonists are isoproterenol (3,4-dihydroxy-α-[(isopropylamino)-methyl]benzyl alcohol), terbutaline (1-[(3,5-dihydroxyphenyl)-2]-(t-butylamino)ethanol), metaproterenol (1-(3,5-dihydroxyphenyl)-2-isopropylaminoethanol), albuterol (2-(t-butylamino)-1-(4-hydroxy-3-hydroxymethylphenyl)-ethanol and the like.

For purposes of the invention, the term "subthreshold bronchodilating effective amount" means a dosage of the indicated material which is insufficient to elicit clinically effective (observable) bronchodilation in a mammal, when such dosage is administered by a particular route.

For example, albuterol is a clinically effective bronchodilator when administered by oral inhalation at a dosage of 180 micrograms (mcg). Thus, for purposes of the invention, the subthreshold bronchodilating effective amount of albuterol when administered by oral inhalation would be an amount less than 180 mcg.

Those skilled in the art will appreciate that the "subthreshold bronchodilating effective amount" will consist of a range of doses, and that there will be a lower limit to said amount below which, the present invention will not operate. For purposes of this invention, this lower limit or minimum dosage may be considered to be about 5% of the effective dose of the particular component.

The subthreshold bronchodilating effective amount whether for forskolin, a particular forskolin derivative or for a particular beta adrenergic agonist will be variable and will depend on, inter alia, the potency of the particular material, the particular route of administration, the combination being administered and the age, size and condition of the patient being treated as well as on the severity of the disease state. The choice of the optimum subthreshold. bronchodilating effective amount for each component is therefore best left to the trained clinician attending a particular patient. Further, administration is best begun at dosage levels which are considered less than optimum and then adjusted as dictated by the needs of the particular patient.

The following subthreshold bronchodilating effective amounts of forskolin and albuterol (both exemplary constituent medicaments of the invention) are given merely for purposes of guiding the clinician in instituting therapy. The inhalation route for both medicaments has been chosen as being exemplary of a clinically useful route of administration:
forskolin 50 mcg to 5000 mcg;
albuterol 5 mcg to 180 mcg.

The forskolin or forskolin derivative component of the invention may be administered either separately from or in combination with the beta adrenergic agonist component of the invention. Any convenient, therapeutically useful route of administration may be utilized. Further, the components may be administered by different routes and at different times for purposes of efficacy and/or convenience.

Thus, for example, a combined dosage form suitable for administration by the inhalation route which comprises 200–2000 mcg forskolin and 5–150 mcg albuterol may be administered four times a day or as required. Alternately, the beta adrenergic agonist component may be administered separately by inhalation, oral or by the intravenous route and the forskolin or forskolin derivative may be administered by the inhalation route. This latter regimen allows additional flexibility in administering the components since each component may be administered on an independent time scale in order to provide an optimal effect.

The components of the invention can be administered in conventional oral dosage forms such as capsules, tablets, pills, powders, suspensions or solutions prepared with conventional pharmaceutically acceptable excipients and additives, using conventional techniques. Parenteral preparations, i.e. sterile solutions or suspensions are also made by conventional means. Inhalation administration can be in the form of a nasal or oral spray. Insufflation is also contemplated. Topical dosage forms can be creams, ointments, lotions and the like. Other dosage forms which can be utilized are transdermal devices and suppositories.

The following test procedure was utilized to assess the usefulness of subthreshold bronchodilating effective amounts of the components of the invention for inhibiting bronchospasm.

Male Hartley guinea pigs were killed with a blow to the head and the trachea removed and cut into segments. Each segment was suspended in an organ bath containing 10 ml of warmed (32° C.) Krebs-Henseleit-bi-carbonate buffer gassed with 95% $O_2$, 5% $CO_2$. The tissue was allowed to equilibrate for 30 minutes to a 1–2 gram tension, recorded isometrically with a Grass TF.03 pressure transducer. Addition of forskolin or albuterol to the tissue caused a dose related relaxation with $EC_{50}$ values of $2.6 \times 10^{-7}$ and $7.6 \times 10^{-8}$ M, respectively. At a subthreshold concentration of $1 \times 10^{-8}$ M, forskolin alone produced 6% relaxation, while albuterol alone produced 18% relaxation. A combination of $1 \times 10^{-8}$ M forskolin with $1 \times 10^{-8}$ M albuterol produced 79% relaxation.

We claim:
1. A method for inducing bronchodilation in a mammal which comprises administering:
   (a) a subthreshold bronchodilating effective amount of forskolin or a forskolin derivative chosen from those having the structural formula I,

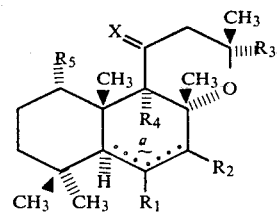

wherein $R_1$ and $R_2$ may be the same or different and are $=O$, H, or $OR_{11}$ wherein $R_{11}$ is H, carboxylic acyl having from 1 to 6 carbon atoms or

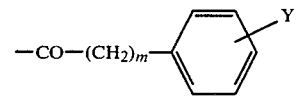

wherein m is 0, 1, 2 or 3 and Y is hydrogen, halogen, alkyl having from 1 to 6 carbon atoms, alkoxy having from 1 to 6 carbon atoms, alkylthio having from 1 to 6 carbon atoms, OH, $CF_3$, $NO_2$, CN, phenyl, benzyl, phenoxy or $NR_aR_b$ wherein $R_a$ and $R_b$ are the same or different and are H or alkyl having from 1 to 6 carbon atoms;
   $R_1$ and $R_2$ when together may form

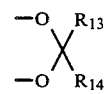

wherein $R_{13}$ and $R_{14}$ may be the same or different and are H, alkyl having from 1 to 6 carbon atoms, alkenyl having from 2 to 6 carbon atoms, alkynyl having from 2 to 6 carbon atoms or

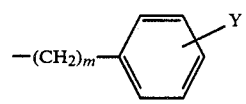

wherein m and Y are defined above;
   $R_3$ is hydrogen; alkyl having from 1 to 10 carbon atoms; $CH_2OH$; CHO; $CO_2R_{15}$ wherein $R_{15}$ is H or alkyl having from 1 to 6 carbon atoms;
   $-CH=CR_{16}R_{17}$ wherein $R_{16}$ is H, halogen, alkyl having from 1 to 6 carbon atoms,

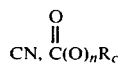

wherein n is O or 1 and $R_c$ is H, alkyl having from 1 to 6 carbon atoms, 1 phenyl or benzyl, CHOHR$_c$ or C(OR$_d$)$_2$R$_c$ wherein R$_c$ is defined above and R$_d$ is alkyl having from 1 to 6 carbon atoms, $R_{17}$ is H, alkyl having from 1 to 6 carbon atoms, alkoxy having from 1 to 6 carbon atoms, benzyl, phenyl or halogen;

—C≡C—$R_{18}$ wherein $R_{18}$ is H, alkyl having from 1 to 12 carbon atoms, alkoxy having from 1 to 6 carbon atoms or

wherein Y is defined above;

—CHOH—C≡C—$R_{19}$ wherein $R_{19}$ is H, alkyl of from 1 to 6 carbon atoms, phenyl or benzyl;

—CH=C=CHR$_{19}$ wherein $R_{19}$ is defined above;

—CH=N—OR$_{19}$ wherein $R_{19}$ is defined above;

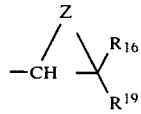

wherein Z is O or S, and $R_{16}$ and $R_{19}$ are defined above;

—CH(ZR$_{20}$)$_2$ wherein Z is defined above and $R_{20}$ is alkyl having from 1 to 6 carbon atoms, phenyl, benzyl or the two groups $R_{20}$ may together form —(CH$_2$)$1_p$—wherein p is 2 or 3;

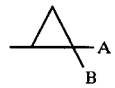

wherein A and B are H, halogen, alkyl having from 1 to 6 carbon atoms, phenyl, benzyl or

wherein n and $R_c$ are defined above;
—CH=N—NDE wherein D and E are H, alkyl having from 1 to 6 carbon atoms, benzyl, phenyl, CoG, SO$_2$G wherein G is alkyl having form 1 to 6 carbon atoms, benzyl or phenyl;

$R_4$ is H or OH;

$R_5$ is OH; or when $R_4$ and $R_5$ are taken together they may form

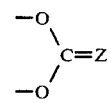

wherein Z is defined above;

a is an optional bond which may be located in either the 5, 6 or 6, 7 position; and X is O or H/OH; and (b) a subthreshold bronchodilating effective amount of a beta adrenergic agonist chosen from among isoproterenol, terbutaline, metaproterenol and albuterol; to said mammal.

2. The method defined in claim 1 wherein $R_1$ and $R_2$ may be the same or different and are OR$_{11}$ wherein $R_{11}$ is defined in claim 1 and Y is hydrogen;

$R_3$ is —CH=CHR$_{30}$ wherein $R_{30}$ is hydrogen, alkyl having from 1 to 6 carbon atoms, phenyl, benzyl or CO$_2$R$_c$;

—C≡CR$_{30}$;

—CHOH—C≡C—$R_{30}$;

—CH=N—OR$_{30}$;

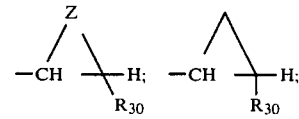

wherein $R_c$ is defined in claim 1 and $R_{30}$ is defined above and

—CH=N—NHR$_{31}$ wherein $R_{31}$ is hydrogen, alkyl having from 1 to 6 carbon atoms, phenyl, benzyl, SO$_2$R$_{32}$ wherein $R_{32}$ is alkyl from 1 to 6 carbon atoms; $R_4$ is H or OH; a is either not present or is located in the 5, 6 position in which instance $R_1$ is H and $R_2$ is OR$_{11}$ is defined hereinabove;

Y is hydrogen; and

X is O.

* * * * *